United States Patent [19]

Yasuda et al.

[11] Patent Number: 5,358,639
[45] Date of Patent: Oct. 25, 1994

[54] METHOD OF ANALYZING HEMOGLOBINS

[75] Inventors: Kenji Yasuda, Tokyo; Yoshinori Takata, Chiba; Harumi Tsuruta, Ibaraki; Sadabumi Ohnuma; Junkichi Miura, both of Hitachi, all of Japan

[73] Assignee: Hitachi, Ltd., Tokyo, Japan

[21] Appl. No.: 38,396

[22] Filed: Mar. 29, 1993

[30] Foreign Application Priority Data

Apr. 1, 1992 [JP] Japan .................................. 4-079508

[51] Int. Cl.⁵ ............................................. B01D 15/08
[52] U.S. Cl. ............................................. 210/635; 210/656; 210/198.2; 436/66; 436/67; 436/161; 530/385; 530/416
[58] Field of Search ............... 210/656, 635, 198.2; 436/66, 67, 161; 530/385, 413, 416, 417

[56] References Cited

U.S. PATENT DOCUMENTS 4,810,391  3/1979  Bruegger ...................... 210/198.2
4,879,039  11/1989  Takahashi ........................ 210/656

FOREIGN PATENT DOCUMENTS 563865  10/1993  European Pat. Off. .......... 210/198.2
63-75558  4/1988  Japan .............................. 210/198.2

OTHER PUBLICATIONS

PTO Translation of Japan Patent 63–75558 by Y. O. on Mar. 16, 1994.

*Primary Examiner*—Ernest G. Therkorn
*Attorney, Agent, or Firm*—Kenyon & Kenyon

[57] ABSTRACT

In the analysis of hemoglobins in blood samples by chromatography, an increase in the pressure in a flow passage line is suppressed, a separation column is made durable against prolonged use by supplying phosphate-based buffer solutions as eluting solutions to a separation column to a separation column and a solution containing not more than 100 mM of S-(carboxyalkyl)-L-cysteine and phosphate-based buffer agent thereto in the course of a series of analyzing steps.

3 Claims, 2 Drawing Sheets

METHOD OF ANALYZING HEMOGLOBINS

BACKGROUND OF THE INVENTION

1. Field of the Invention

The present invention relates to a method and an apparatus for analyzing hemoglobins, and a solution for suppressing deterioration of a separation column for use therein, and particularly to techniques suitable for analyzing hemoglobins in blood samples by liquid chromatography.

2. Related Background Art

It is the conventional practice to analyze glycohemoglobins in blood samples by liquid chromatography for diagnosis of diabetes, etc.

Japanese Patent Application Kokai (Laid-open) No. 63-75558 discloses such conventional practice, where glycohemoglobins in blood samples are analyzed by supplying a potassium phosphate buffer solution as an eluting solution to a separation column provided with carboxyl groups as ion exchange groups.

Chromatographic separation of blood samples by a phosphate-based buffer solution in a separation column provided with carboxyl groups, etc. as ion exchange groups, as in the above-mentioned conventional practice, has the following problem. When operations to separate glycohemoglobins, etc. are repeated in the same liquid chromatographic analyzing apparatus so as to conduct analyzing treatments of a large number of blood samples, the pressure in the flow passage line of the analyzing apparatus is gradually increased to lower the separability of sample components. Such an increase in the pressure and decrease in the separability are due to deterioration of the separation column.

Thus, when the liquid chromatographic analyzing apparatus for analyzing glycohemoglobins, etc. is used for a prolonged time, the deteriorated separation column must be exchanged with a fresh one. Heretofore, exchange frequency of such deteriorated separation columns is so high that the operator suffers from many troublesome works for the exchange with increasing consumption of the separating columns.

SUMMARY OF THE INVENTION

An object of the present inventions is to provide a novel means capable of suppressing an increase in the pressure in the flow passage line in the analyzing apparatus during chromatography of hemoglobins and of maintaining a high component separability for a prolonged time.

Another object of the present invention is to provide a method and an apparatus for analysis capable of suppressing deterioration of a separation column provided with carboxyl groups or carboxyalkyl groups as ion exchange groups, and a solution for suppressing column deterioration.

These objects can be attained by supplying a phosphate-based buffer solution containing not more than 100 mM of S-(carboxyalkyl)-L-cysteine to a separation column when hemoglobins in blood samples are analyzed by supplying a phosphate-based buffer solution as an eluting solution to the separation column. The solution can be used as an eluting solution for separating blood sample components or as a washing solution (regenerating-solution) for a separation column after the component separation.

DETAILED DESCRIPTION OF THE INVENTION

It is known that blood contains hemoglobins, glycohemoglobins, hemoglobin F, etc. as hemoglobin-related substances. The term "hemoglobins" will be used hereinafter to refer to those hemoglobin-related substances.

A separation column for liquid chromatography for use in the analysis of hemoglobins is packed with granular fillers with specific exchange groups bonded to a matrix material. As a matrix material, polymers such as polyvinyl alcohol, polymethacrylate, etc. or silica are used. As ion exchange groups, carboxyl groups, carboxymethyl groups, etc. are used.

In elution of hemoglobins from a separation column, multi-step elution (usually three-step elution), where a plurality of eluting solutions are stepwise supplied, or gradient elution, where pH of an eluting solution is gradually changed, is used to shorten the treating time. As an eluting solution, a system using a plurality of solutions containing a potassium phosphate buffer agent (a mixture of potassium dihydrogen phosphate and dispotassium hydrogen phosphate), a system using a plurality of solutions containing a sodium phosphate buffer agent (a mixture of sodium dihydrogen phosphate and disodiumhydrogen phosphate), or a system using a selected combination of these two former systems is used. Anyway, phosphate-based buffer solutions are used as eluting solutions.

Any of the eluting solutions is prepared to have a pH of preferably 5.5 to 6.5, but a plurality of eluting solutions prepared to have a pH of 5.5 to 7.5 can be used, when desired. In case of multi-step elution, the last step eluting solution is prepared to contain 1 to 10 mM of S-(carboxyalkyl)-L-cysteine. In case of gradient solution, an eluting solution containing at least 1 mM of S-(carboxyalkyl)-L-cysteine is supplied to the separation column in the latter half period of the entire elution course. In any case, a solution containing at least 1 mM of S-(carboxyalkyl)-L-cysteine is supplied to the separation column after the A1(one)c component of hemoglobins has been eluted from the separation column.

The solution containing S-(carboxyalkyl)-L-cysteine can be used not only as an eluting solution, but also as a column washing solution. In that case, the column washing solution is a phosphate-based buffer solution adjusted to a pH of 5.0 to 6.5, and contains a phosphate-based buffer agent as a main component and 5 to 100 mM of S-(carboxyalkyl)-L-cysteine.

It is practical to use S-(carboxymethyl)-L-cysteine (which will be hereinafter referred to as "S-CMC") as an S-(carboxyalkyl)-L-cysteine. S-(carboxyethyl)-L-cysteine can be also used to give the similar effect. For convenience of explanation, description Will be made hereinafter, referring only to S-CMC as a typical example of S-(carboxyalkyl)-L-cysteine. Even if S-CMC is added alone to an eluting solution or a column washing solution, an effect of suppressing deterioration of a separation column can be obtained, though depending on the kind of contamination of the separation column. The effect of suppressing the deterioration of a separation column can be much more enhanced by adding S-CMC to an eluting solution or a column washing solution together with a surfactant.

As a surfactant to be added to an eluting solution or a washing solution together with S-CMC, a surfactant capable of easily bonding to protein or lipid is used. For example, polyoxyethylene (10) octyl ether as one of nonionic surfactants has a strong tendency to bond mainly to protein. Such a surfactant is commercially available from Rohm & Haas Co., U.S.A., as Triton X-100 (trademark). Dodecyl-N-betaine as one of amphoteric surfactants has a strong tendency to bond mainly to lipid. Such a surfactant is commercially available from Kao K.K., Japan as Amphitol 24B (trademark).

When blood samples are introduced into a liquid chromatographic analyzing apparatus and subjected to repeated eluting operations not on the basis of the present invention, contaminants contained in the blood samples, such as protein, lipid, polysaccharides, polynucleotide, etc. are adsorbed onto the surfaces of fillers in the separation column, and are gradually accumulated thereon with increasing number of the blood samples introduced. Thus, the function of ion exchange groups of the fillers is gradually deteriorated and the pressure at the inlet side of the separation column is also gradually increased. Component separability of the separation column is lowered with progressing deterioration of the separation column, and ultimately the separation column must be exchanged with a fresh one.

When the present invention is applied to liquid chromatography of blood samples by supplying a solution containing S-CMC and surfactants as a last step eluting solution, for example, of a three-step elution, to a separation column, contaminants such as protein, lipid, etc. are hardly adsorbed onto the surfaces of fillers in the separation column with a very small decrease in the pressure in the flow passage line even if the eluting operations are repeated, and the component separability can be maintained at a high level for a prolonged time. This means that S-CMC works as an agent for suppressing deterioration of a separation column.

Still furthermore, a solution containing both S-CMC and surfactants works to liberate contaminants once bonded to the filler surfaces and remove them from the filler surfaces, that is, it works to regenerate the once deteriorated separation column to a reusable state. A solution containing surfactants and not S-CMC hardly remove the contaminants once bonded to the filler surfaces. Thus, a solution containing both S-CMC and surfactants can be used as a treating solution for regenerating the deteriorated separation column.

A solution containing not less than 1 mM of S-CMC has tendency to deteriorate separation of glycohemoglobin components, but a solution containing less than 1 mM of S-CMC has a less effect of suppressing deterioration of a separation column. Thus, a solution containing not less than 1 mM of S-CMC is supplied to the separation column after glycohemoglobin components such as A1(one)a, A1(one)b, A1(one)c, etc. have been eluted from the separation column. A solution containing less than 1 mM of S-CMC has substantially no adverse effect on the separation of glycohemoglobin components, and thus S-CMC can be added to all the eluting solutions at such a low concentration.

A solution containing more than 10 mM of S-CMC has an adverse effect on the separation of hemoglobin components (Ao component). Thus, an eluting solution must be prepared to contain not more than 10 mM of S-CMC. When S-CMC is added to a column washing solution, on the other hand, the concentration can be increased to about 100 mM. In that case, there is no fear of direct influence on the component separation, but it is necessary to purge the column washing solution from the washed separation column with a first step eluting solution containing no S-CMC before the next blood sample is introduced into the separation column. Higher the concentration of S-CMC, the stronger the action of desorbing the contaminants from the filler surfaces and the shorter the treating time with the column washing solution.

PREFERRED EMBODIMENTS OF THE INVENTION

Embodiments of the present invention will be explained below.

Figure 1:
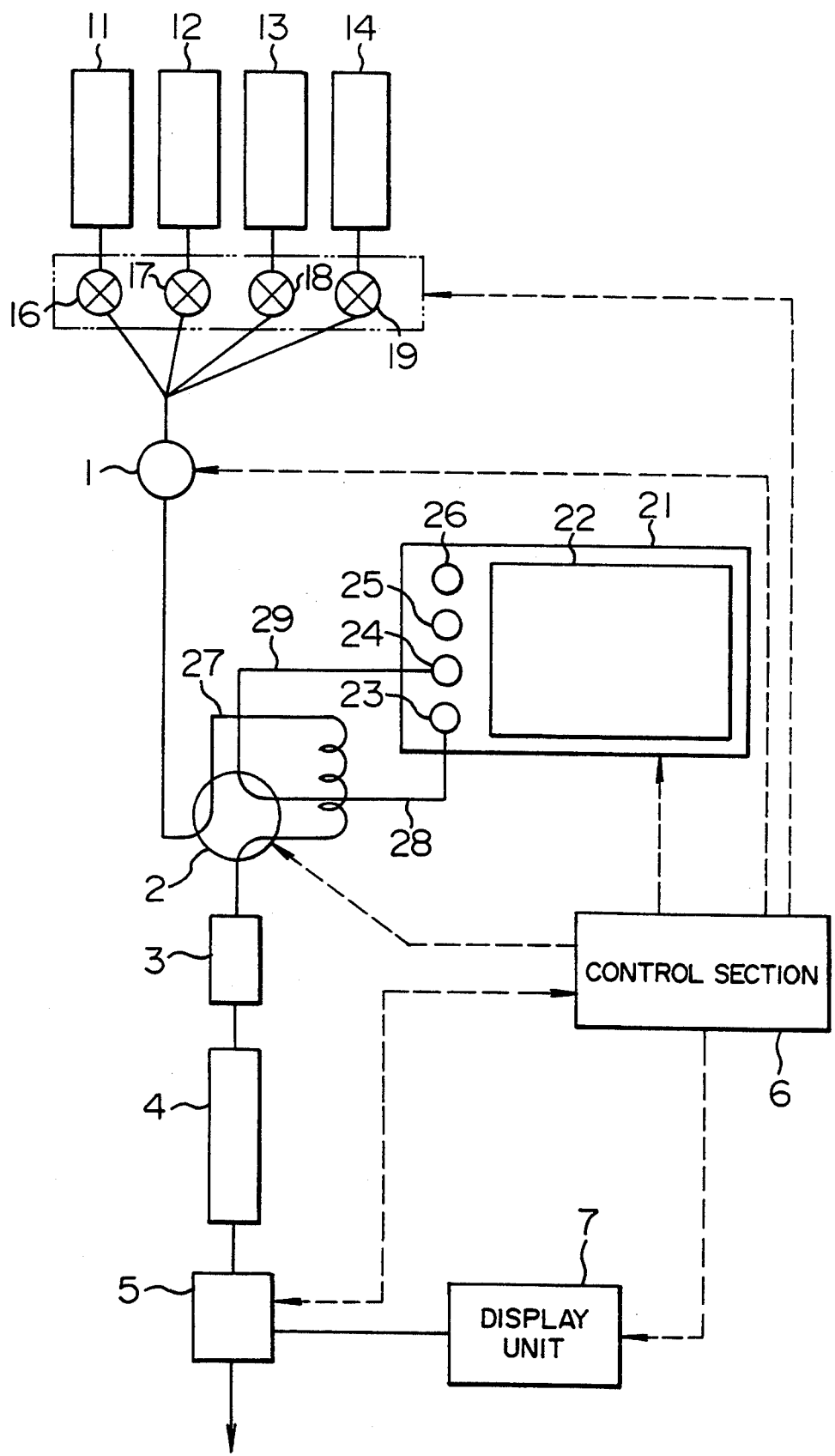
FIG. 1 is a schematic flow diagram outlining the structure of a liquid chromatographic analyzing apparatus according to the present invention.

Structure of a liquid chromatographic analyzing apparatus for analyzing hemoglobins in blood is outlined in FIG. 1 where three-step elution is carried out.

In FIG. 1, an eluting solution to be pumped at a predetermined flow rate of 0.5 to 10 ml/min by a feed pump 1 is supplied to a separation column 4 through a sampling valve 2 having a constant volume tube 27 and a flow passage filter 3. A blood sample introduced from the sampling valve 2 is separated into components in the separation column 4, and the eluted components are detected by a detector 5 comprising an ultraviolet-visible light absorption photometer. The thus obtained chromatogram is displayed on a display unit 7. Peaks of the individual components detected by the detector 5 are subjected to a computation treatment in a control section 6, and the results of the computation treatment are displayed with component names, retention time of each peak, component concentration of each peak, etc. on the display unit 7.

An eluting solution tank 11 contains a first step eluting solution, an eluting solution tank 12 a second step elution solution and an eluting solution tank 13 a last step eluting solution. A washing solution tank 14 contains a washing solution and is used, when required. In the ordinary analyzing operations, eluting steps for each sample, using only the eluting solution tanks 11 to 13, are repeated. Individual tanks 11 to 14 are provided with valves 16 to 19 correspondingly, and opening or closing motions of these valves are carried out with timing according to a predetermining program instructed from the control section 6. Activation of feed pump 1, sampling valve 2, detector 5, autosampler 21, etc. is also controlled according to a predetermined program from the control section 6.

An autosampler 21 has a detachable sample rack 22, on which maximum 100 sample containers can be placed. As the sample containers, vacuum blood sampling tubes can be used as such in the ordinary case. The autosampler comprises a sample injection port 23, a drain port 24, a dilution vessel 25, and a washing port 26. The injection port 23 is connected to the sampling valve 2 through a flow passage line 29. The autosampler 21 further has a conveying mechanism capable of moving in both directions X and Y, a pipette nozzle capable of moving freely in the horizontal direction over the autosampler 21 and moving vertically at a desired position by the conveying and a syringe mechanism communicated with the pipette nozzle.

Blood samples are pretreated in the autosample 21 before introduction into the sampling valve 2. At first, a predetermined amount of a whole blood sample in one sample container is sampled into the pipette nozzle and discharged into the dilution vessel 25. Successively, the nozzle is washed by the washing port 26, and a dilution solution is discharged into the dilution vessel 25 from the nozzle to dilute the blood to 160 times the original volume to uniformly disperse the blood therein. A portion of the blood sample diluted in the dilution vessel 25 is sampled by the nozzle and fed into the constant-volume tube 27 of the sampling valve 2 from the sample injection port 23. When the constant-volume tube 27 is filled with the blood sample, the sampling valve 2 is switched over to convey the constant volume of the sample to the separation column 4 by the passing stream of the eluting solution.

The separation column 4 is packed with granular fillers with carboxyl groups or carboxyalkyl groups bonded as ion exchange groups to the matrix material. The separation column 4 has such sizes as an inner diameter of about 4 to about 6 mm and a length of about 30 to about 80 mm. A flow cell in the detector 5 is made of quartz glass and has a light path length of 3 to 10 mm. When an ultraviolet-visible photometer is used as the detector 5, light having a wavelength of 410 nm is detected as light for the sample and light having a wavelength of 530 nm is detected as light for reference.

Figure 2:
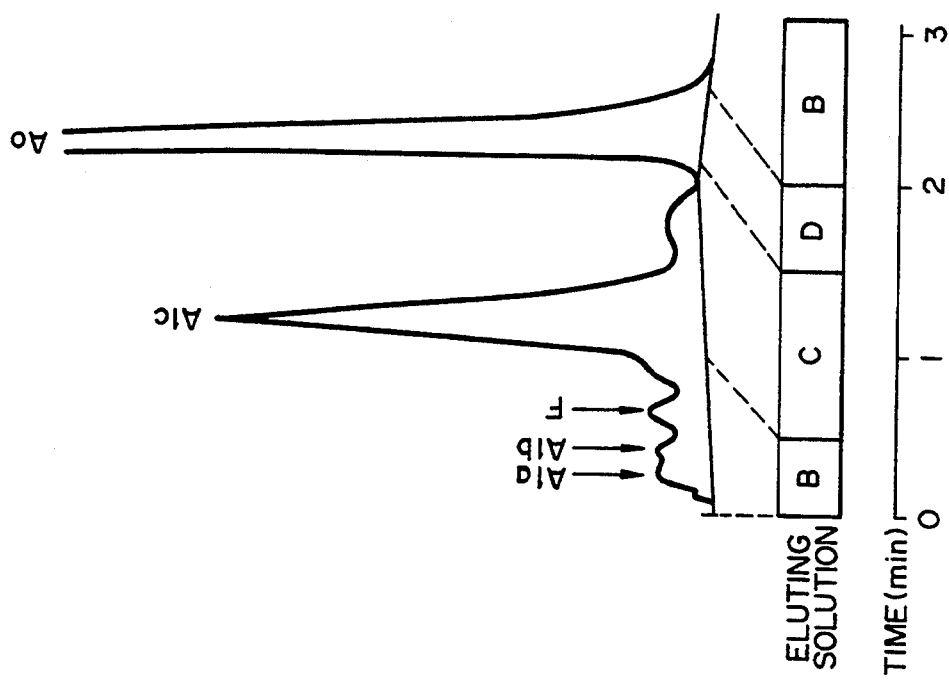
FIG. 2 is a diagram showing an example of supplying eluting solution for the analysis of hemoglobins.

When the time of sample injection is made to be a starting time, eluting solutions are supplied as shown in FIG. 2, in case of 3-step elution without using a washing solution. That is, an eluting solution B is supplied from the first step eluting solution tank 11, an eluting solution C from the second step eluting solution tank 12, and an eluting solution D from the third step eluting solution tank 13. At the starting time, the eluting solution B is supplied to the separation column 4, and 0.6 minutes after the starting time, the eluting solution C is supplied thereto. 1.6 minutes after the starting time, the eluting solution D is supplied thereto, and 2.0 minutes after the starting time, the eluting solution B is supplied thereto to make the separation column ready for the introduction of the next sample. In this example, the time required for one sample is 3.3 minutes, and such eluting solution supplying operators are repeated according to the sample-introducing timing program.

In the example of FIG. 2, the last step eluting solution D contains S-CMC and a surfactant, and in every sample-introducing cycle, the fillers in the separation column 4 are cleaned by the reagent for suppressing the deterioration of the separation column 4, as contained in the eluting solution D. The timing for introducing the last step eluting solution D is just after the A1(one)c component peak has been eluted from the separation column. Even if supply of the eluting solution D is started by opening the valve 18 according to instructions from the control section 6 1.6 minutes after the starting time, the eluting solution D starts to flow out of the separation column 4 about 2 minutes after the starting time, as shown by dotted line in FIG. 2.

Glycohemoglobin components such as peaks A1(one)a, A1(one)b, A1(one)c, unstable A1(one)c (not shown in the drawing), etc. and hemoglobin F component as peak F have been already eluted from the separation column 4 before the eluting solution D containing S-CMC is supplied to the separation column. However, peaks Ao as a hemoglobin component is eluted by the eluting solution D.

Examples of the analyzing method will be given below.

EXAMPLE 1

Hemoglobins in blood samples were analyzed by the analyzing apparatus of FIG. 1. Separation column 4 was packed with fillers having carboxymethyl groups as ion exchange groups. Particle sizes of the fillers were 5 μm. Feed rate of feed pump 1 was set to 1.4 ml/min. Three kinds of eluting solutions shown in the following Table were used as eluting solutions, and supply of the eluting solution was switched over stepwise according to the program as shown in FIG. 2, without using a washing solution.

TABLE

| Eluting solution | Composition | | | pH |
|---|---|---|---|---|
| 1st step eluting solution | $KH_2PO_4$ | 50.3 | mM | 6.23 |
|  | $K_2HPO_4$ | 10.7 | mM |  |
|  | Triton X-100 | 0.02 | wt. % |  |
|  | Amphitol 24B | 0.02 | wt. % |  |
| 2nd step eluting solution | $KH_2PO_4$ | 59.6 | mM | 6.22 |
|  | $K_2HPO_4$ | 12.7 | mM |  |
|  | Triton X-100 | 0.02 | wt. % |  |
|  | Amphitol 24B | 0.02 | wt. % |  |
| 3rd step eluting solution | $NaH_2PO_4$ | 144 | mM | 6.20 |
|  | $Na_2HPO_4$ | 50.1 | mM |  |
|  | S-CMC | 2 | mM |  |
|  | Triton X-100 | 0.02 | wt. % |  |
|  | Amphitol 24B | 0.02 | wt. % |  |

Comparison was made between a case not based on the present invention and a case based on the present invention. In the case not based on the present invention the same first step eluting solution and the second step solution as shown in the foregoing Table were used, whereas the same third step eluting solution as shown in the foregoing Table, except that no S-CMC was contained therein was used, as the eluting solutions.

Figure 3B:
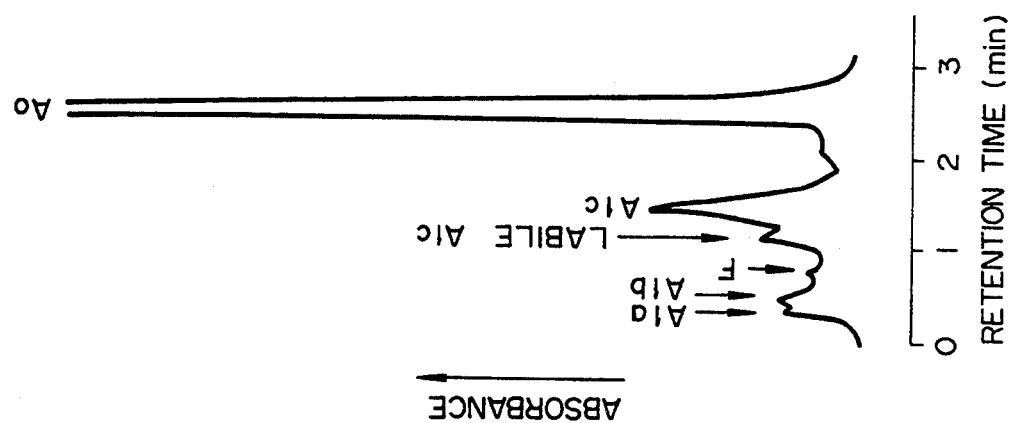
FIG. 3A and FIG. 3B are chromatograms effect of the present invention.
Figure 3A:
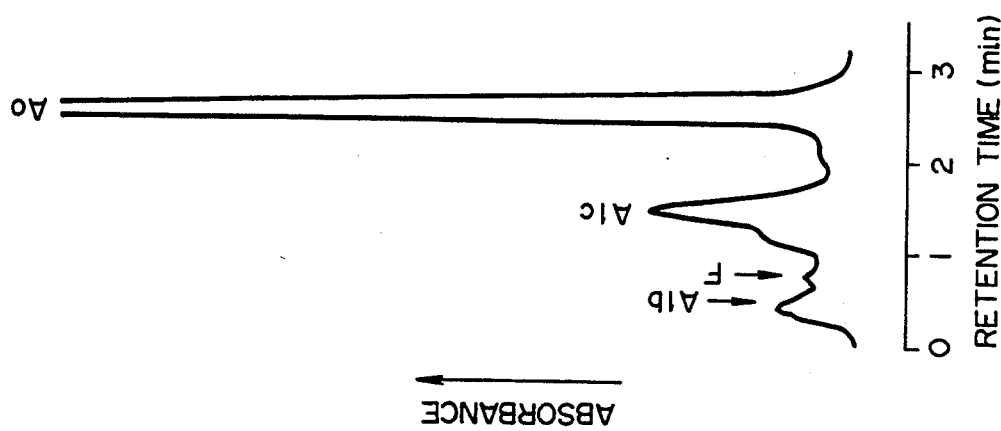

Eluting operations were carried out continuously with both groups of the eluting solutions each for 1,000 blood samples. In the case not based on the present invention, a chromatogram as shown in FIG. 3A was obtained, whereas in the case based on the present invention, a chromatogram as shown in FIG. 3B was obtained.

When 1,000 samples were continuously treated not on the basis of the present invention, pressure at the inlet side of the separation column 4 was increased to 70 bars from the original 50 bars. As is obvious from FIG. 3A, separation around the A1(one)b peak was poor and the A1(one)a peak that must have been properly present was not identified. Furthermore, separation around the A1(one)c peak was poor and the peak of unstable A1(one)c (L-A1(one)c) was not identified. That is, only 4 components could be identified. Furthermore, the retention time for obtaining the chromatograms had a tendency to become a little shorter at the later runs than that at the earlier runs.

In the case base on the present invention, the chromatograms obtained even after the continuous treatments of 1,000 samples were not substantially changed from those obtained at the earlier runs. Pressure at the inlet side of the separation column was increased only to 45 bars from the initial 50 bars. As is obvious from FIG. 3B, A1(one)b peak and A1(one)a peak were separated from each other, and A1(one)c peak and labile A1(one)c peak were separated from each other. That is, the 6 components could be identified, and this shows that deterioration of the separation column was very small. Retention time for obtaining the chromatograms at the later runs was not substantially changed from that at the earlier runs. It was found that continuous treatments of even 10,000 samples could be carried out in the present invention, while keeping a high separability.

EXAMPLE 2

To analyze hemoglobins in blood samples in the analyzing apparatus of FIG. 1, fillers with carboxyl groups as ion exchange groups and having particle sizes of 5 μm were packed in the separation column. The first to third step eluting solutions were buffer solutions each containing disodium hydrogen phosphate and sodium dihydrogen phosphate and having a pH of 5.94 for the first step, a pH of 5.82 for the second step and a pH of 5.71 for the third step. In this example, a column washing solution was used besides the eluting solutions.

The washing solution placed in the washing solution tank 14 of FIG. 1 was a phosphate based buffer solution containing the same main components as in the eluting solutions, and further containing 20 mM of S-CMC and 0.5% by weight of Triton X-100 (surfactant) on the basis of the solution, adjusted to pH 5.65.

The column washing solution containing S-CMC was supplied to the separation column 4 after the third step eluting solution, and a predetermined time after the supply the column washing solution was switched to the first step eluting solution to obtain a column equilibrium for the next sample. When the column washing solution was used besides the eluting solutions, deterioration of the separation column could be suppressed by adding S-CMC and the surfactant in a column washing solution, whereby an increase in the pressure of the separation column subjected to repeated use for a prolonged time could be suppressed and a high separability could be maintained, resulting in improved reproducibility of exact analysis of hemoglobins.

EXAMPLE 3

A separation column packed with fillers with carboxymethyl groups as ion exchange groups and having particle sizes of 7 μm was used, and a reagent for suppressing deterioration of the separation columns was added to a third step eluting solution as a last step eluting solution and no column washing solution was used. The first step eluting solution was a sodium phosphate-based buffer solution having a pH of 5.92, the second step eluting solution was a potassium phosphate-based buffer solution having a pH of 7.25, and the third step buffer solution was a sodium phosphate-based buffer solution having a pH of 5.95 and containing 5 mM of S-CMC and 0.2% by weight of Triton X-100 on the basis of the solution. In this example, an increase in the pressure of the separation column could be suppressed in the analysis of hemoglobins.

EXAMPLE 4

Function to regenerate the separability of deteriorated separation column by a reagent for suppressing the deterioration of a separation column was tested. In the separation column, which treated 1,000 blood samples not on the basis of the present invention, component separability was deteriorated, as shown in FIG. 3A. With the thus deteriorated separation column, hemoglobins in blood samples were analyzed by repeatedly supplying the eluting solutions shown in the foregoing Table to the separation column. Approximately at the 15th cycle after supplying the eluting solutions shown in the foregoing Table thereto, improvement of component separability could be observed in the chromatograms. Approximately at the 30th cycle, 6 components could be identified, and approximately at the 100th cycle, substantially the same separatability as the original one could be obtained. That is, the same chromatograms as that shown in FIG. 3B could be obtained.

In the present invention, hemoglobins can be analyzed for a prolonged time while suppressing an increase in the pressure in the flow passage line, and thus suppression of deterioration of a separation column can be attained with improved reproducibility of analytical results.

What is claimed is:

1. A method for analyzing hemoglobins in blood samples by supplying phosphate-based buffer solutions as an eluting solution to a separation column provided with carboxyl groups or carboxyalkyl groups as ion exchange groups, which comprises supplying a solution containing S-(carboxyalkyl)-L-cysteine and a phosphate based buffer agent to the separation column.

2. A method to claim 1, wherein the solution containing the S-(carboxyalkyl)-L-cysteine and a surfactant, adjusted to a pH of 5.5 to 7.5, is used as one of eluting solutions.

3. A method according to claim 2, wherein the solution is supplied to the separation column after glycohemoglobin components have been eluted from the separation column.

* * * * *

UNITED STATES PATENT AND TRADEMARK OFFICE
CERTIFICATE OF CORRECTION

PATENT NO. : 5,358,639
DATED : 25 October 1994
INVENTOR(S) : Kenji YASUDA et al.

It is certified that error appears in the above-indentified patent and that said Letters Patent is hereby corrected as shown below:

IN THE TITLE PAGE, in line 6 of Abstract: Delete "to a separation column".

| Column | Line | Corrections |
|--------|------|-------------|
| 1 | 37 | After "etc." insert --,--. |
| 1 | 41 | After "columns" change "is" to --was--; after "that" insert --it caused--; after "operator" replace "suffers from many" with --to do an excess of--. |
| 1 | 42 | Change "works" to --work--. |

UNITED STATES PATENT AND TRADEMARK OFFICE
CERTIFICATE OF CORRECTION

PATENT NO. : 5,358,639
DATED : 25 October 1994
INVENTOR(S) : Kenji YASUDA et al.

It is certified that error appears in the above-indentified patent and that said Letters Patent is hereby corrected as shown below:

| Column | Line | |
|---|---|---|
| 2 | 23 | Change "dis-" to -- di- --. |
| 2 | 27 | Change "disodumhydrogen" to --disodium hydrogen--. |
| 2 | 55 | Change "Will" to --will--. |
| 4 | 3 | Change "Higher" to --The higher--. |
| 6 | 1 | Change "is" to --are--. |
| 6 | 61 | Change "base" to --based--. |
| 6 | 66 | Change "45" to --54--. |

Signed and Sealed this

Twentieth Day of May, 1997

BRUCE LEHMAN

Attest:

Attesting Officer

Commissioner of Patents and Trademarks